(12) United States Patent
Desouches et al.

(10) Patent No.: US 10,143,060 B2
(45) Date of Patent: Nov. 27, 2018

(54) LIGHTING EQUIPMENT WITH OPTIMUM STIMULATION OF NON-VISUAL FUNCTIONS

(71) Applicants: MAQUET SAS, Orleans (FR); INSERM, Paris (FR); ENTPE, Vaulx en Velin (FR)

(72) Inventors: Jerome Desouches, Orleans (FR); David Le Ber, Chaingy (FR); Claud Gronfier, Lyons (FR); Dominique Dumortier, Venissieux (FR); Pascale Avouac, Villeurbanne (FR); Howard Cooper, Collonges au Mont D'or (FR)

(73) Assignees: Maquet SAS, Ardon (FR); Inserm, Paris (FR); Entpe, Vaulx en Velin (FR)

( * ) Notice: Subject to any disclaimer, the term of this patent is extended or adjusted under 35 U.S.C. 154(b) by 0 days.

(21) Appl. No.: 15/548,802

(22) PCT Filed: Jan. 27, 2016

(86) PCT No.: PCT/FR2016/050164
§ 371 (c)(1),
(2) Date: Aug. 4, 2017

(87) PCT Pub. No.: WO2016/124836
PCT Pub. Date: Aug. 11, 2016

(65) Prior Publication Data
US 2018/0020523 A1    Jan. 18, 2018

(30) Foreign Application Priority Data

Feb. 5, 2015  (FR) ...................................... 15 50896

(51) Int. Cl.
*H05B 37/02*    (2006.01)
*H05B 33/08*    (2006.01)
(Continued)

(52) U.S. Cl.
CPC ......... *H05B 33/0872* (2013.01); *A61B 90/30* (2016.02); *A61B 90/36* (2016.02);
(Continued)

(58) Field of Classification Search
CPC ............ H05B 33/0857; H05B 33/0872; H05B 37/0218; H05B 37/0227; H05B 37/0272; H05B 37/0281
(Continued)

(56) References Cited

U.S. PATENT DOCUMENTS 6,548,967 B1 * 4/2003 Dowling ............ G06Q 30/0201
                                                    315/318
8,624,505 B2 * 1/2014 Huang ................ F21V 23/0457
                                                    315/118
(Continued)

FOREIGN PATENT DOCUMENTS

EP    2 051 763 A2    4/2009
JP    2002169493 A    6/2002
(Continued)

OTHER PUBLICATIONS

Chellappa, et al; "Photic memory for executive brain responses"; PNAS; vol. 111, No. 16; Apr. 22, 2014; pp. 6087-6091.
(Continued)

*Primary Examiner* — Tung X Le
(74) *Attorney, Agent, or Firm* — Ware, Fressola, Maguire & Barber LLP

(57) ABSTRACT

The lighting equipment comprises a lighting device with a plurality of light sources for delivering white light having a tunable light spectrum, and a monitoring and control device that controls the light sources in a modulation cycle for modulating the light spectrum, which cycle comprises a first period where the light spectrum is red-enriched, a second period where the light spectrum is gradually modulated from
(Continued)

red to blue, a third period where the light spectrum is blue-enriched, and a fourth period where the light spectrum is modulated gradually from blue to red. The control device is arranged to detect reception of a signal indicating a human presence, and, in response, reinitializes the modulation cycle when the modulation cycle is in the first period, or gradually modulates the light spectrum from blue to red when the modulation cycle is in the second, third or fourth period before reinitializing the modulation cycle.

21 Claims, 3 Drawing Sheets

(51) Int. Cl.
*A61M 21/00* (2006.01)
*A61B 90/00* (2016.01)
*A61N 5/06* (2006.01)
*A61B 90/30* (2016.01)

(52) U.S. Cl.
CPC ........... *A61M 21/00* (2013.01); *A61N 5/0618* (2013.01); *H05B 33/0857* (2013.01); *H05B 37/029* (2013.01); *H05B 37/0227* (2013.01); *H05B 37/0281* (2013.01); *A61B 2090/309* (2016.02); *A61M 2021/0044* (2013.01); *A61M 2205/13* (2013.01); *A61M 2205/3306* (2013.01); *A61M 2205/3375* (2013.01); *A61M 2205/609* (2013.01); *A61M 2205/6054* (2013.01); *A61N 2005/0626* (2013.01); *A61N 2005/0629* (2013.01); *A61N 2005/0651* (2013.01); *A61N 2005/0663* (2013.01)

(58) Field of Classification Search
USPC .................................. 315/152, 307, 312, 360
See application file for complete search history.

(56) References Cited

U.S. PATENT DOCUMENTS

| | | | |
|---|---|---|---|
| 2010/0217358 A1 | 8/2010 | Herbert et al. | |
| 2012/0068608 A1* | 3/2012 | Covaro | G01J 1/18 315/151 |
| 2012/0095534 A1 | 4/2012 | Schlangen et al. | |
| 2012/0139425 A1* | 6/2012 | Kim | F21S 2/005 315/152 |
| 2012/0262575 A1* | 10/2012 | Champagne | G08B 13/19613 348/143 |
| 2015/0335246 A1* | 11/2015 | Rains, Jr. | F21V 23/003 362/231 |
| 2017/0105265 A1* | 4/2017 | Sadwick | A61N 5/0618 |

FOREIGN PATENT DOCUMENTS

| | | |
|---|---|---|
| JP | 2008276443 A | 11/2008 |
| JP | 2009283317 A | 12/2009 |
| JP | 2010527680 A | 8/2010 |
| JP | 2014220169 A | 11/2014 |
| WO | 02/20079 A1 | 3/2002 |
| WO | 2008/146220 A2 | 12/2008 |
| WO | 2013/011589 A1 | 1/2013 |

OTHER PUBLICATIONS

Mure, et al; "Melanopsin Bistability: A Fly's Eye Technology in the Human Retina"; PLoS ONE; vol. 4, Issue 6; Jun. 2009; pp. 1-10.

* cited by examiner

LIGHTING EQUIPMENT WITH OPTIMUM STIMULATION OF NON-VISUAL FUNCTIONS

CROSS REFERENCE TO RELATED APPLICATIONS

This application is the U.S. National Stage of International Application Number PCT/FR2016/050164 filed on Jan. 27, 2016, which application claims priority under 35 USC § 119 to French Patent Application No. 1550896 filed on Feb. 5, 2015. Both applications are hereby incorporated by reference in their entirety.

The subject matter disclosed herein was developed by, or on behalf of, one or more parties to a joint research agreement and the names of the parties to the joint research agreement are Maquet SAS having a principal place of business at Parc de Limere, Avenue de la Pomme de Pin, 45160 Ardon, France; Inserm having a principal place of business at 101 rue de Tolbiac, 75013, Paris, France; and Entpe having a principal place of business at 3 rue Maurice Audin, 69120 Vaulx En Velin, France.

TECHNICAL FIELD

The field of the invention is the field of lighting equipment, in particular lighting equipment used in surgical operating theaters.

The invention relates more particularly to lighting equipment, in particular for an operating theater, which lighting equipment comprises a lighting device with a plurality of light sources for delivering white light having a tunable light spectrum, and a monitoring and control device that controls the light sources in such a manner as to modulate the light spectrum in a repeatable modulation cycle without interruption, which cycle comprises a first period of time during which the light spectrum is red-enriched, a second period of time during which the light spectrum is gradually modulated from red to blue, a third period of time during which the light spectrum is blue-enriched, and a fourth period of time during which the light spectrum is modulated gradually from blue to red.

PRIOR ART

Most lighting manufacturers propose lighting having a tunable light spectrum. Changing the spectrum takes place by combining a plurality of light sources, each of which has a specific wavelength. Such light sources are generally light-emitting diodes (LEDs) but they can also be fluorescent tubes. Such lighting is generally composed of three or four different light sources respectively offering the colors blue, green, red, and sometimes white. Such lighting generally makes it possible to select a plurality of ambiances via a control panel or a button. Certain modes make it possible to modulate the spectrum over time, the color then going from red to violet, then to blue, then to green, etc. The variation in the spectrum takes place by modulating the current through or the voltage across the terminals of the light sources. Often, however, modulating the spectrum of such lighting serves a purpose that is purely aesthetic.

It is known that surgeons working at night in hospitals suffer, as do most night workers, from disorders affecting vigilance and mood, and from psychomotor degradations during their night shifts. Such deficits are mainly related to poor adaptation (synchronization) of the biological clocks of the staff with respect to nighttime activity, and are described conventionally in the International Classification of Sleep Disorders (ICSD-3), such as Circadian Rhythm Sleep-Wake Disorders.

Today, it is well known that light makes it possible to stimulate attention and cognitive and motor performance in humans, in particular by acting on the non-visual functions (wakefulness, sleep, mood, and biological clock). Document US 2010/0217358 describes, for example, stimulation of wakefulness in humans by artificial light. Documents JP 2009/283317 and WO 2013/11589 describe lighting systems making it possible to improve the performance of a user, those systems modulating the light cyclically from blue to red starting from the blue-enriched light spectrum.

It is also known that a user being exposed to a light spectrum modulation cycle starting with a stage of a few minutes of red-enriched light increases cognitive performance relative to a cycle starting with a stage of blue-enriched light, as described by Mure et al, PloSone2009 and Chellapa et al. PNAS 2014.

Document WO 2008/146220 describes a lighting device that can generate a variable spectrum for creating a biological effect. Document EP 2 051 763 describes a system and a method for influencing a photobiological state of a subject.

If, during a surgical operation, a specific user such as the surgeon enters an operating theater having a lighting system in which the light spectrum modulation cycle has already been initiated and/or if the lighting system is emitting light having a spectrum that is not red-enriched, the stimulation of the surgeon by the light spectrum modulation is less effective.

SUMMARY OF THE INVENTION

An object of the invention is thus to propose lighting equipment with a lighting device having a tunable spectrum that makes it possible to reinforce the cognitive performance and the psychomotor performance of the medical staff in a surgical operating theater all through the night, and more particularly, to reinforce the performance of the surgeons as soon as they enter an operating theater.

To this end, the invention provides lighting equipment, in particular for an operating theater, which lighting equipment comprises a lighting device with a plurality of light sources for delivering white light having a tunable light spectrum, and a monitoring and control device that controls the light sources in such a manner as to modulate the light spectrum in a repeatable modulation cycle without interruption, which cycle comprises a first period of time during which the light spectrum is red-enriched, a second period of time during which the light spectrum is gradually modulated from red to blue, a third period of time during which the light spectrum is blue-enriched, and a fourth period of time during which the light spectrum is modulated gradually from blue to red, the lighting equipment being characterized in that the monitoring and control unit is arranged to detect reception of a signal indicating a human presence in the vicinity of the lighting device, and in that, in response to the signal being detected, the monitoring and control device reinitializes the modulation cycle when the modulation cycle is in the first period of time, or gradually modulates the light spectrum from blue to red during a transient period of time when the modulation cycle is in the second, third or fourth period of time before reinitializing the modulation cycle.

The lighting equipment of the invention may also have the following features:

the first period of time is shorter than the third period of time;

the transient period of time is shorter than the second and fourth periods of time;

the second and fourth periods of time are shorter than the third period of time;

the monitoring and control device is arranged to control the light sources in such a manner as to maintain a constant flux of white light during the variation in the light spectrum of white light;

the proportion of red is greater than the proportion of blue in the light spectrum of white light during the first period of time;

the proportion of blue is greater than the proportion of red in the light spectrum of white light during the third period of time;

the proportions of red and blue in the light spectrum of white light are constant respectively during the first period of time and during the third period of time;

the proportions of blue and red in the light spectrum of white light during the second period of time go gradually from the proportions of blue and red that are present in the light spectrum of white light during the first period of time to the proportions of blue and red that are present in the light spectrum of white light during the third period of time;

the proportions of blue and red in the light spectrum of white light during the fourth period of time go gradually from the proportions of blue and red that are present in the light spectrum of white light during the third period of time to the proportions of blue and red that are present in the light spectrum of white light during the first period of time;

it further comprises at least one presence sensor connected to the monitoring and control device for receiving the signal indicating human presence in the vicinity of the lighting device;

the presence sensor is a contactless sensor for receiving a signal of the infrared, Bluetooth, ultra-sound, radiofrequency or voice type;

the presence sensor is a vision sensor with facial recognition;

the presence sensor is a contact sensor;

the presence sensor recognizes a biometric signature;

the presence sensor is a badge or chip reader;

it comprises two presence sensors spaced apart from each other;

the repeatable modulation cycle is programmable to start and/or to stop automatically as from a predetermined time of the day;

the repeatable modulation cycle is activatable manually by a user;

the repeatable modulation cycle is deactivatable manually by a user; and the light sources are LEDs.

The basic idea of the invention is thus to propose anti-fatigue lighting having repeatable cyclic modulation of a light spectrum so as to maximize the physiological effect of the light and thereby stimulate the vigilance, attention, and cognitive and psychomotor performance of medical staff throughout the night. The effect of light on non-visual functions mainly involves activating retinal ganglion cells containing melanopsin, which cells have a sensitivity peak in blue (lambda max=480 nm). Thus, blue-enriched light is more effective than blue-poor light, because of the sensitivity of the ganglion cells containing melanopsin.

During exposure to light, the photopigment of the cells containing melanopsin absorbs the photons, thereby leading to a physiological response (activation of the brain centers involved in vigilance and cognition). At the same time, that process desensitizes the photopigment and renders it inactive to the other photons. Unlike the photopigments in the cones and rods, which photopigments require a long regeneration process, melanopsin is capable of regenerating its sensitivity by absorbing a second photon, in the red region of the spectrum. This reversibility, known as "bistability", thus enables melanopsin to switch between two states, and thus to be activated by "blue" light and reactivated by "red" light.

That is why the alternation of red-enriched light and of blue-enriched light starting with a first period of red-enriched light maximizes the stimulating effects of the subsequent blue-enriched light.

The lighting equipment of the invention is thus designed to modulate the light spectrum from predominantly red light to predominantly blue light cyclically and without interruption in repeated manner. Very particularly, the attention and performance of a surgeon operating at night or under high sleep pressure conditions, e.g. after long days of work, must be stimulated. Thus, as soon as surgeons enter the operating theater, they must be subjected to the first period of time of exposure to red-enriched light in order to amplify the non-visual effects of the blue-enriched light to which they will be exposed in the third period of time. That is why, as soon as the presence of the surgeon is detected in the vicinity of the lighting device, if the lighting equipment is emitting red-enriched light, then, in response to such detection, the modulation cycle is reinitialized, and, if the lighting equipment is emitting blue-enriched light or a mixture of blue-enriched and red-enriched light, then, in response to such detection, the modulation cycle is interrupted so as to return gradually to the red-enriched light so as to start a modulation cycle again.

BRIEF DESCRIPTION OF THE DRAWINGS

The present invention can be better understood and other advantages appear on reading the following description and on examining the accompanying drawings, in which.

DESCRIPTION OF EMBODIMENTS

Figure 1:
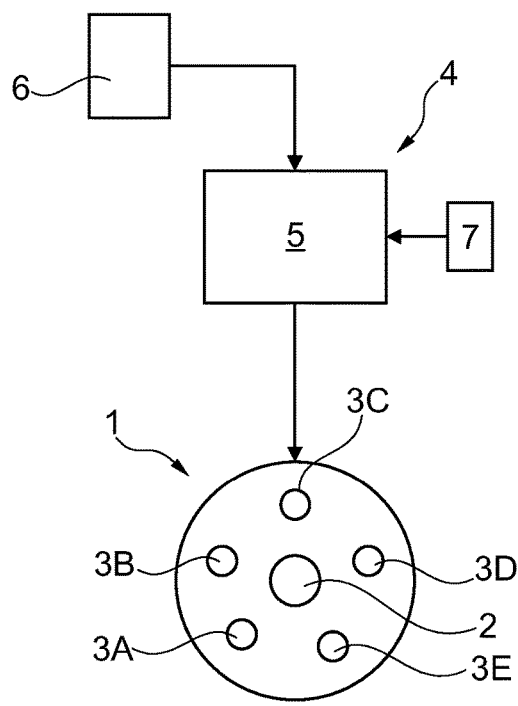
FIG. 1 shows an embodiment of a lighting set of the invention.

In FIG. 1, the light spectrum modulation lighting set of the invention includes a lighting device 1 having a plurality of light sources, which, in this example, are LEDs 2, 3A to 3E. The lighting device 1 may be controlled by means of an electronic monitoring and control device 4.

A plurality of lighting devices such as the lighting device 1 may be implemented in the lighting set recessed in the ceiling of a room such as an operating theater, or suspended, e.g. via an articulated suspension arm.

In the lighting device 1, LED 2 produces white light of arbitrary color temperature and color rendering index (CRI), LED 3A produces blue-enriched light with a radiation peak lying in the range 440 nanometers (nm) to 520 nm, and LED 3B produces red-enriched light with a radiation peak lying in the range 570 nm to 660 nm.

For example, LED 2 diffuses white light at a color temperature in the region of 4400 kelvins (K). In accordance with the invention, this white light is mixed with the light produced by LEDs 3A and 3B under the monitoring of the monitoring and control device 4 that individually controls the current fed to these LEDs.

The monitoring and control device 4 includes, in particular, a control unit 5 of the microprocessor type that is controlled by the user of the lighting set via a button or a keypad (not shown), and a program memory 6.

When the type of light ambience is chosen by the user, the control unit 5 runs a program recorded in the memory 6 for controlling the LEDs 3A and 3B in such a manner as to generate a plurality of light ambiences corresponding to different light spectra of the white light produced by the lighting device 1.

In particular, in accordance with the invention, the control unit 5 causes the white light spectrum to follow a modulatable cycle that is repeatable without interruption. The modulation cycle includes a period of time during which the light spectrum is red-enriched and a period of time in which the light spectrum is blue-enriched, with, between those periods, a gradual modulation of the light spectrum from red to blue or from blue to red.

In order to reduce the fatigue of the user, the stimulating effect of the predominantly blue light is used throughout the night. Predominantly blue light, punctuated by periods during which the light is predominantly red, makes it possible to regenerate the ganglion cells containing melanopsin. That is why it is advantageous to be able to modulate the light spectrum cyclically between predominantly blue and predominantly red. In addition, a preliminary exposure to red-enriched light, prior to an exposure to blue-enriched light, makes it possible to increase the effects of the blue-enriched light on the non-visual functions of the user. Thus, in accordance with the invention, as soon as the lighting set is switched on, the light spectrum modulation cycle commences with a period of exposure to red-enriched light.

Figure 2:
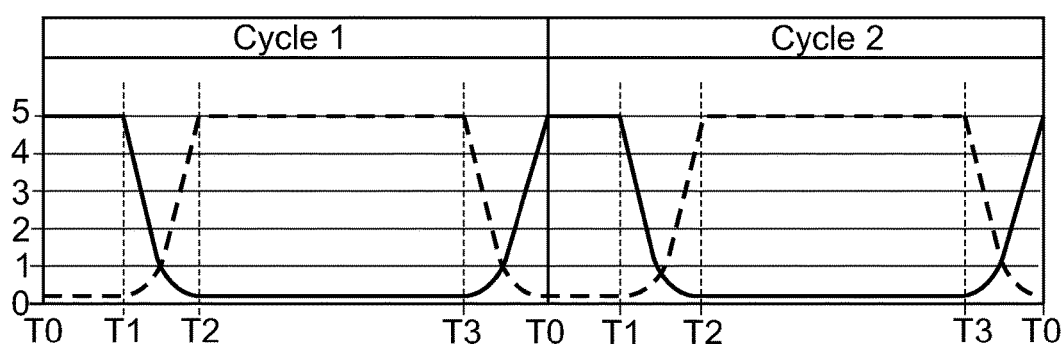
FIG. 2 shows two successive modulation cycles for modulating the light spectrum.

FIG. 2 shows two successive modulation cycles for modulating the blue and red components of the light spectrum, the uninterrupted line representing the red-to-blue ratio, and the dashed line representing the blue-to-red ratio. On initialization T0 of the cycle, the light spectrum is red-enriched and remains red-enriched for a first period of time T0-T1 that may, for example, last for in the range 2 minutes to 10 minutes.

The first period of time T0-T1 is followed by a second period of time T1-T2 during which the light spectrum goes gradually from red to blue. In order to avoid disturbing the visual comfort of the users, the second period of time T1-T2 may last for 5 minutes, for example.

At the end of the second period of time T1-T2, the light spectrum is blue-enriched. It remains blue-enriched for a third period T2-T3 that may, for example, lie in the range 10 minutes to 20 minutes.

A fourth period of time T3-T0 is the last stage of a modulation cycle, during which stage the light spectrum goes gradually from blue to red, e.g. in about 5 minutes. Once one cycle ends, a second cycle can begin automatically, and so on.

Figure 3:
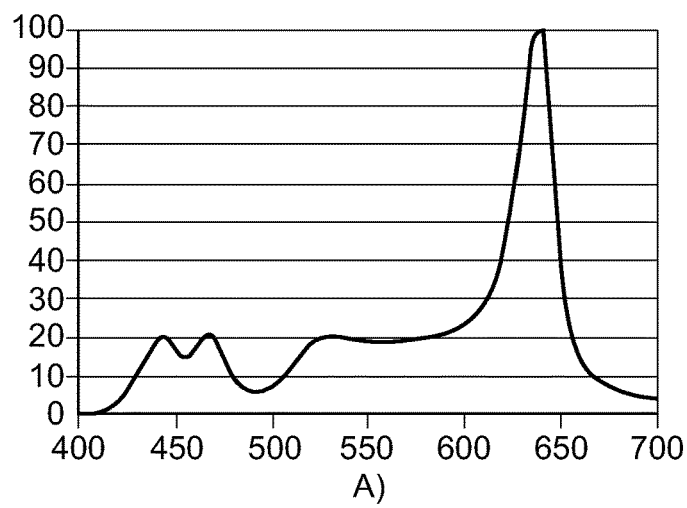
FIG. 3 shows three graphs, each of which shows a light spectrum during the modulation cycle for modulating the light spectrum generated by the lighting set of the invention; on each graph of FIG. 3, the wavelength is plotted along the abscissa axis and the radiometric power of the light as normalized at 100 is plotted up the ordinate axis.
Figure 3:
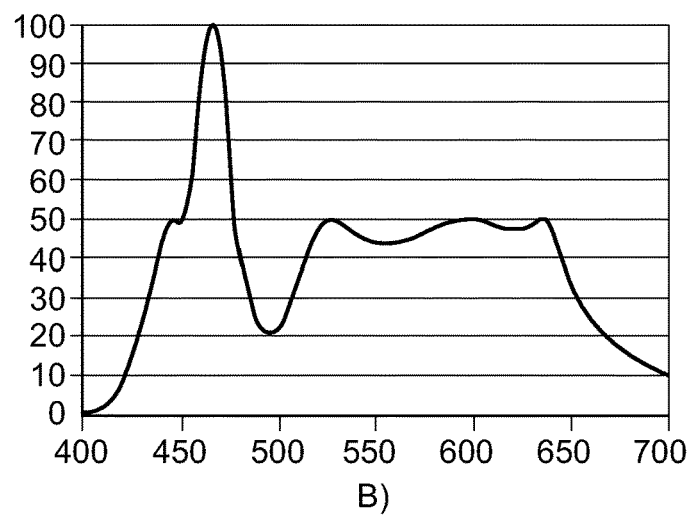
Figure 3:
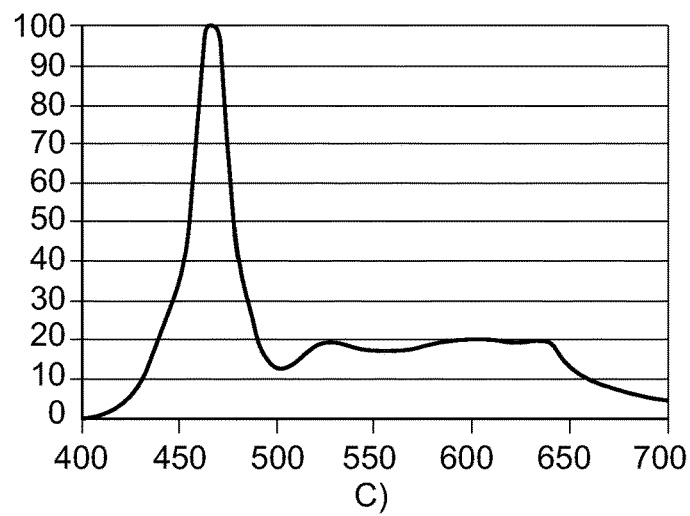

When the light spectrum goes from red to blue, or from blue to red, in order for the change not to be perceptible by the user and not to impair user comfort, the control unit 5 may generate gradual transitions in the spectrum, from blue to red, and from red to blue. Thus, the control unit 5 generates a multitude of intermediate spectra between the blue-enriched spectrum and the red-enriched spectrum and vice versa, as shown in FIG. 3. Each intermediate spectrum is close to the two spectra that are adjacent to it and is generated over a minimum observation time for the eye of the user.

In accordance with the invention, a cycle as described above can last in the range 10 minutes to several hours, the optimum duration lying in the range 22 minutes to 40 minutes. Preferably, the first period of time T0-T1 is shorter than said third period of time T2-T3. The second and fourth periods of time T1-T2 and T3-T0 are shorter than the third period of time.

Graph A) of FIG. 3 shows a red spectrum generated during the first period of time of the modulation cycle. Graph B) of FIG. 3 shows an intermediate spectrum between red and blue that is generated during the second period during which the modulation is gradual. Graph C) of FIG. 3 shows a blue spectrum generated during the third period of time of the modulation cycle.

It should be understood that during the second period of time T1-T2 of the modulation cycle, the control unit 5 gradually decrements the proportion of red while also gradually increasing the proportion of blue. During the fourth period of time T3-T0 of the modulation cycle, the control unit 5 gradually increases the proportion of red and gradually decrements the proportion of blue.

During a surgical operation, a surgeon must, very particularly, be attentive and perform well. This is why the visual stimulation offered by the lighting set of the invention must be optimum for the surgeon as soon as said surgeon arrives in the operating theater. Thus, if the surgeon enters the operating theater while the lighting set is emitting blue-enriched light or a mixture of blue-enriched and red-enriched light, the effects of amplification of the non-visual responses to blue light will be smaller for the surgeon. It is therefore important to be able to identify surgeons and to detect their presence so that they receive optimum visual stimulation as soon as they enter the operating theater.

For this purpose, in accordance with the invention, the lighting equipment includes a presence sensor 7 connected to the monitoring and control device 4. Said presence sensor 7 is suitable for receiving a signal indicating a human presence, such as the presence of a certain person, namely the surgeon in this example. The presence sensor 7 may be a contactless sensor that receives a signal by infrared, Bluetooth, ultra-sound, or radiofrequency, or a contact sensor, such as a mechanical button on which the surgeon presses, or indeed a sensor that recognizes a biometric signature, such as a fingerprint.

The sensor may be a vision sensor for facial recognition, but it may also be a sensor for voice recognition.

The sensor may be a card reader or a chip reader.

For example, when locating a radiofrequency identification (RFID) chip is used, a presence sensor may be placed on the floor at the thresholds of the doors or of the airlock of the operating theater. In order to determine the direction in which the surgeon is going past, two sensors may be positioned, one in the operating theater and one in the corridor. In which case, the surgeon identification part could be placed in the surgeon's shoe, e.g. in the sole. Without limiting the scope of the invention, other sensors may be added in order to improve determination of the direction in which the surgeon is going past.

In another embodiment, an operating table can also be equipped with a RFID sensor for detecting the presence of the surgeon within its radius of action.

In accordance with the invention, as soon as a signal indicating the surgeon is entering the operating theater is detected, if the lighting equipment is emitting red-enriched light then the control unit 5 of the monitoring and control unit 4 reinitializes the modulation cycle; if the lighting equipment is emitting blue-enriched light or a mixture of blue-enriched and red-enriched light, the modulation cycle is interrupted so as to return gradually over a transient period of time to red-enriched light so as to start a normal modulation cycle again. It can be understood that, during the transient period of time, the control unit 5 gradually increases the proportion of red and gradually decrements the proportion of blue. However, so that the surgeon is not exposed to an initial spectrum that is not red-enriched, said transient period of time must be short.

In the event that the surgeon needs to leave the operating theater, the signal indicating the surgeon's presence in the vicinity of the lighting device is no longer detected, but the modulation cycle will continue normally. If the surgeon comes back into the operating theater, the monitoring and control device 4 detects, once again, a signal indicating the surgeon is present and the above-described procedure is reproduced.

In another embodiment, a plurality of surgeons could be identified, and each of them would send a signal indicating that they are present in the vicinity of the lighting device.

Figure 4:
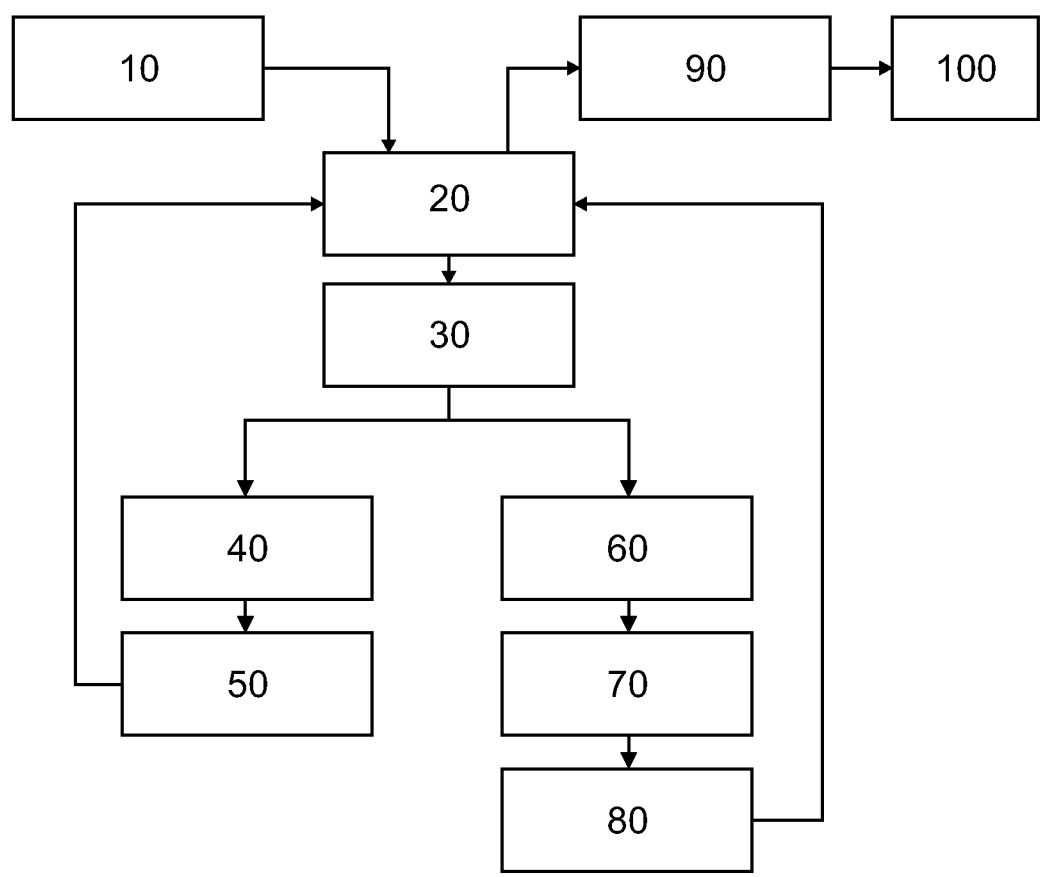
FIG. 4 shows operation of the monitoring and control device.

FIG. 4 shows how the control unit 5 operates. It is started at 10, e.g. by actuation of the keypad. The control unit 5 is programmed to set itself to the predominantly red spectrum when the lighting set is actuated and, in step 20, it generates the first modulation cycle regardless of whether or not the signal indicating the presence of the surgeon is received by the presence sensor 7 connected to the control unit 5. It repeats said modulation cycle in looped manner, e.g. throughout the duration of the surgical operation, or throughout the night, and stops the process if, for example, it receives a command to stop operating or to change operating mode.

If, at step 30, the monitoring and control device 4 detects reception of a signal indicating the presence of the surgeon in the vicinity of the lighting device 1, then, in accordance with the invention:

- if the light spectrum at step 40 is red-enriched, then, in step 50, the control unit 5, causes the modulation cycle to be reinitialized without modifying the light spectrum, so as to return to step 20; and
- if the light spectrum at step 60 is blue-enriched or is a mixture of blue and red, then, in step 70, the control unit 5 causes the light spectrum emitted to undergo a gradual transition towards the red-enriched light spectrum, and then causes the modulation cycle for modulating the light spectrum to be reinitialized at step 80 so as to return to step 20.

Step 90 corresponds to the moment when the presence sensor no longer receives any signal, and the modulation cycle continues until the lighting equipment is switched off or possibly until the program is deactivated.

At step 70, corresponding to the above-mentioned transient period of time, it is advantageous to increase the speed of transition relative to the normal speed of gradual modulation, i.e. during an undisturbed modulation cycle. This increase in speed, during this transient period of time, should not disturb the work and the comfort of the medical staff already present in the operating theater while also making it possible to decrease a time of exposure of the surgeon to the initial non-red spectrum. This transient period of time is generally shorter than the second and third periods of time T1-T2 and T3-T0.

It should be noted that a manual or programmed operating mode may be deactivated manually in favor of another operating mode, making it possible, for example, to choose a particular color for the emitted light.

When an operating mode is more particularly intended for night workers, it can be programmed to be deactivated during the day, e.g. from 7 a.m. to 7 p.m., for example, and to be activated automatically as from a certain time, e.g. 7 p.m. However, if a user wishes to activate this operating mode during the day, the user may do so.

In accordance with the invention, the various light spectra may be recorded in the program memory 6 in the a form usable by the control unit 5 for controlling the current in the LEDs 2, 3A, 3B.

In addition to the blue and red lights produced by the LEDs 3A and 3B, it is also possible to mix the white light with yellow, green, and cyan lights, for example, produced by other LEDs 3C, 3D, 3E shown in FIG. 1. These LEDs 3C to 3E are also controlled by the control unit 5 and serve, for example, for improving the color rendering index.

For example, on the graph A) of FIG. 3, the enrichment color is red. It can be seen that the ratio of radiometric power between blue and red is 20%. Similarly, the ratio of radiometric power between green and red is 20%.

On graph C) in FIG. 3, it can be seen, up the ordinate axis, that the radiometric power of green represents 20% of the radiometric power of blue at 100%, which, in this example is the enrichment color. It can also be seen on graph C) that the radiometric power of red represents 20% of the radiometric power of blue.

Graph B) shows the transition for going from a predominantly red spectrum to a predominantly blue spectrum, while maintaining a radiometric power of at least 20% between the wavelength of the enrichment color component and each wavelength of the other color components in the white light spectrum.

In order to maintain a good color rendering index, it should be understood that the lights produced by the LEDs 3C 3D, 3E are modulated gradually to follow the incrementation of the red or blue component in the cycle.

It should be noted that the control unit 5 is arranged to maintain a constant lighting power independently of the modulation cycle for modulating the light emitted by the lighting set, e.g. by means of a flux sensor (not shown) disposed in the lighting device 1 and that sends back a flux measurement for servo-controlling the current in the LEDs. Thus, the monitoring and control device (4) controls the light sources (2, 3A-3E) in such a manner as to maintain a constant flux of white light during the modulation of the light spectrum of white light.

Naturally, the present invention is in no way limited to the above description of one of its embodiments, which can undergo modifications without going beyond the ambit of the invention.

The invention claimed is:

1. A lighting equipment, in particular for an operating theater, comprising:
    a lighting device with a plurality of light sources for delivering white light having a tunable light spectrum, and
    a monitoring and control device that controls said light sources so as to modulate said light spectrum in a repeatable modulation cycle without interruption, which cycle comprises a first period of time during which said light spectrum is red-enriched, a second period of time during which said light spectrum is gradually modulated from red to blue, a third period of time during which said light spectrum is blue-enriched, and a fourth period of time during which said light spectrum is modulated gradually from blue to red, wherein said monitoring and control device is configured to detect reception of a signal indicating a human presence in the vicinity of said lighting device, and in response to said signal being detected, said monitoring and control device reinitializes said modulation cycle when said modulation cycle is in said first period of time, or gradually modulates said light spectrum from blue to red during a transient period of time when said modulation cycle is in said second, third or fourth period of time before reinitializing said modulation cycle.

2. The lighting equipment according to claim 1, wherein said first period of time is shorter than said third period of time.

3. The lighting equipment according to claim 1, wherein said transient period of time is shorter than said second and third periods of time.

4. The lighting equipment according to claim 1, wherein said second and fourth periods of time are shorter than said third period of time.

5. The lighting equipment according to claim 1, wherein said monitoring and control device is arranged to control said light sources so as to maintain a constant flux of white light during said modulation of said light spectrum of white light.

6. The lighting equipment according to claim 1, wherein the proportion of red is greater than the proportion of blue in said light spectrum of white light during said first period of time.

7. The lighting equipment according to claim 1, wherein the proportion of blue is greater than the proportion of red in said light spectrum of white light during said third period of time.

8. The lighting equipment according to claim 1, wherein the proportions of red and blue in said light spectrum of white light are constant respectively during said first period of time and during said third period of time.

9. The lighting equipment according to claim 1, wherein the proportions of blue and red in said light spectrum of white light during said second period of time go gradually from the proportions of blue and red that are present in said light spectrum of white light during said first period of time to the proportions of blue and red that are present in said light spectrum of white light during said third period of time.

10. The lighting equipment according to claim 1, wherein the proportions of blue and red in said light spectrum of white light during said fourth period of time go gradually from the proportions of blue and red that are present in said light spectrum of white light during said third period of time to the proportions of blue and red that are present in said light spectrum of white light during said first period of time.

11. The lighting equipment according to claim 1, wherein the lighting equipment further comprises a presence sensor connected to said monitoring and control device for receiving said signal indicating human presence in the vicinity of said lighting device.

12. The lighting equipment according to claim 11, wherein said presence sensor is a contactless sensor for receiving a signal of the infrared, Bluetooth, ultra-sound, radiofrequency or voice type.

13. The lighting equipment according to claim 11, wherein said presence sensor is a vision sensor with facial recognition.

14. The lighting equipment according to claim 11, wherein said presence sensor is a contact sensor.

15. The lighting equipment according to claim 14, wherein said presence sensor recognizes a biometric signature.

16. The lighting equipment according to claim 11, wherein said presence sensor is a badge or chip reader.

17. The lighting equipment according to claim 11, wherein the lighting equipment includes two presence sensors spaced apart from each other.

18. The lighting equipment according to claim 1, wherein the repeatable modulation cycle is programmable to start and/or to stop automatically as from a predetermined time of the day.

19. The lighting equipment according to claim 1, wherein the repeatable modulation cycle is activatable manually by a user.

20. The lighting equipment according to claim 1, wherein the repeatable modulation cycle is deactivatable manually by a user.

21. The lighting equipment according to claim 1, wherein said light sources are LEDs.

* * * * *